US010464133B2

(12) United States Patent
Danger et al.

(10) Patent No.: US 10,464,133 B2
(45) Date of Patent: Nov. 5, 2019

(54) METHOD FOR PRODUCING A MEDICAL INSTRUMENT BY WAY OF AN ADDITIVE METHOD

(71) Applicant: Gebr. Brasseler GmbH & Co. KG, Lemgo (DE)

(72) Inventors: Karl-Heinz Danger, Detmold (DE); Michael Kuellmer, Lemgo (DE); Frank Hagemann, Lemgo (DE)

(73) Assignee: Gebr. Brasseler GmbH & Co. KG, Lemgo (DE)

( * ) Notice: Subject to any disclaimer, the term of this patent is extended or adjusted under 35 U.S.C. 154(b) by 613 days.

(21) Appl. No.: 15/120,883

(22) PCT Filed: Jan. 26, 2015

(86) PCT No.: PCT/EP2015/051500
§ 371 (c)(1),
(2) Date: Aug. 23, 2016

(87) PCT Pub. No.: WO2015/128139
PCT Pub. Date: Sep. 3, 2015

(65) Prior Publication Data
US 2016/0361765 A1    Dec. 15, 2016

(30) Foreign Application Priority Data
Feb. 26, 2014   (DE) .................. 10 2014 203 458

(51) Int. Cl.
*B22F 3/10* (2006.01)
*B22F 3/105* (2006.01)
*A61C 3/00* (2006.01)
*A61C 3/02* (2006.01)
*A61C 3/06* (2006.01)
*A61C 3/12* (2006.01)
*A61B 17/16* (2006.01)
*B33Y 80/00* (2015.01)
*B23K 26/342* (2014.01)
*A61C 3/03* (2006.01)
*B22F 3/24* (2006.01)
*B23D 65/00* (2006.01)
*B23K 15/00* (2006.01)
*B23K 26/362* (2014.01)
*B23K 26/38* (2014.01)
*B23P 15/32* (2006.01)
*B23P 15/34* (2006.01)
*B28B 1/00* (2006.01)
*B29C 64/153* (2017.01)
*B22F 5/00* (2006.01)
*B33Y 10/00* (2015.01)
*A61B 17/00* (2006.01)

(52) U.S. Cl.
CPC ........ *B22F 3/1055* (2013.01); *A61B 17/1615* (2013.01); *A61C 3/00* (2013.01); *A61C 3/02* (2013.01); *A61C 3/03* (2013.01); *A61C 3/06* (2013.01); *A61C 3/12* (2013.01); *B22F 3/24* (2013.01); *B23D 65/00* (2013.01); *B23K 15/0086* (2013.01); *B23K 26/342* (2015.10); *B23K 26/362* (2013.01); *B23K 26/38* (2013.01); *B23P 15/32* (2013.01); *B23P 15/34* (2013.01); *B28B 1/001* (2013.01); *B29C 64/153* (2017.08); *B33Y 80/00* (2014.12); *A61B 2017/00526* (2013.01); *A61B 2017/1602* (2013.01); *B22F 2003/247* (2013.01); *B22F 2005/001* (2013.01); *B22F 2998/10* (2013.01); *B33Y 10/00* (2014.12); *Y02P 10/295* (2015.11)

(58) Field of Classification Search
CPC .......... B22F 3/10; B22F 3/1055; B33Y 80/00; B23K 26/342; B29C 64/153; A61B 17/1615; A61C 3/00; A61C 3/02
USPC .......................................... 419/28
See application file for complete search history.

(56) References Cited

U.S. PATENT DOCUMENTS

| 7,261,550 B2 | 8/2007 | Herzog |
| 8,946,585 B2 | 2/2015 | Kappmeyer |
| 2008/0131479 A1 | 6/2008 | Weber et al. |
| 2012/0213659 A1 | 8/2012 | Bayer et al. |

FOREIGN PATENT DOCUMENTS

| DE | 19901643 A1 | 7/2000 |
| DE | 102006026967 A1 | 12/2007 |
| DE | 102010048090 A1 | 4/2012 |
| DE | 102012000466 B3 | 4/2013 |
| WO | WO2004004955 A1 | 1/2004 |
| WO | WO2007010598 A1 | 1/2007 |

(Continued)

OTHER PUBLICATIONS

International Search Report and Written Opinion dated Apr. 17, 2015 for counterpart PCT application No. PCT/EP2015/051500.

(Continued)

*Primary Examiner* — Edward M Johnson
(74) *Attorney, Agent, or Firm* — Shuttleworth & Ingersoll, PLC; Timothy J. Klima

(57) ABSTRACT

A method for producing a medical instrument, includes producing, by cutting material from a semi-finished product, a shaft including a clamping region and at least part of a head including cutting edges; additively generating at least part of the head of the instrument; performing the additively generating with a rotation axis of the instrument aligned vertically; reworking at least part of the head with a subtractive method; and using the subtractive method to perform at least one chosen from sharpening cutting edges and improving concentric running of the instrument.

6 Claims, 2 Drawing Sheets

(56) References Cited

FOREIGN PATENT DOCUMENTS

WO     WO2011026164 A1     3/2011
WO     2013149697 A2     10/2013

OTHER PUBLICATIONS

European Office Action dated Feb. 12, 2019 from counterpart European App 15702693.1.
German Office Action dated Oct. 23, 2014 from counterpart German App 102014203458.2.

METHOD FOR PRODUCING A MEDICAL INSTRUMENT BY WAY OF AN ADDITIVE METHOD

This application is the National Phase of International Application PCT/EP2015/051500 filed Jan. 26, 2016 which designated the U.S.

This application claims priority to German Patent Application 102014203458.2 filed Feb. 26, 2014, the entirety of which is incorporated by reference herein.

Medical instruments, for example dental drills, milling cutters, grinding instruments, sonic tips or saw blades, are classically produced in the prior art by cutting methods. These methods usually start out from a semi-finished product which is machined by cutting in different work steps. In particular, the production of cutting edges or toothed arrangements is carried out by milling or grinding.

The classical production methods have the disadvantage that they are suitable only for certain geometries. For example, it is not possible to produce undercuts or cavities, since the geometry of the instrument is directly related to the production methods and the tools used.

The development of such instruments is therefore limited to some extent by the production methods that are available.

The object of the invention is to make available a method for producing a medical instrument, which method avoids the disadvantages of the prior art and permits precise and cost-effective production.

The object is achieved by a combination of features disclosed herein, while further advantageous embodiments are set forth in the present disclosure.

According to the invention, provision is thus made that the medical instrument is produced by means of an additive production method. This additive production method can be used, according to the invention, either for the whole instrument or for part thereof, for example for a head provided with cutting edges.

The additive production methods permitting the production of medical instruments, for example from steel, ceramic, hard metal, titanium or plastic, usually start out from a powdered material. The latter is melted on in layers, for example by laser or electron beam. It is therefore a production method that does not use tools. It follows from this that the geometry, for example of a head of a dental milling cutter provided with cutting edges, is not limited by the tools that are to be used in production. Instead, it is possible to produce cavities, undercuts, irrigation channels, aeration channels or the like in a single work step by means of the additive method.

The medical instruments in question are for the most part very small components (in particular dental drills or dental milling cutters). The amount of material to be applied additively is therefore small. This affords the possibility of high batch numbers being able to be produced very quickly and therefore very cost-effectively.

The production method according to the invention is suitable both for individual production of a single instrument and also for simultaneous production of a large number of instruments in a common device for additive production.

In the additive or generative production method to be used according to the invention, provision is thus made for a medical instrument to be produced layer by layer, with the layers directly structured and overlapping. It is particularly expedient if the instrument is produced in a vertical arrangement. In this way, particularly in the case of rotary instruments, it is possible to produce them rotationally symmetrically with respect to a rotation axis, such that there is no need for re-working. Moreover, with a vertical arrangement, it is possible to do without the formation of support areas, which would subsequently have to be removed again.

According to the invention, the additive production preferably takes place using a powder material or the like. The instrument is built up layer by layer in a container filled with the powder. The respective upper layer of powder is generated by selective laser fusion, selective laser sintering, by electron beam welding or by a DLD technique. Thereafter, the next layer of powder is applied, wherein the powder is melted on and solidified in the exact shape to generate the instrument by means of the laser or electron beam or in some other way. Customary layer thicknesses are between 20 μm and 100 μm.

The additive production methods permit production of medical instruments whose mechanical properties correspond substantially to those of the base material used. High component densities are obtained, which can be almost 100%. It follows from this that the instruments produced according to the invention have a high degree of strength and, consequently, have a long useful life and provide a good cutting performance.

In a particularly expedient embodiment of the invention, provision is made that the medical instrument is generated in a hybrid set-up. For example, it is possible to produce a shaft with a clamping region by cutting material from a semi-finished product and thereafter, for example, to produce the head provided with the cutting edges, or at least produce part of the head, by an additive method. This type of solution may prove particularly advantageous if the production of a tool, in the area of its shaft and its clamping region, can be performed by automated cutting and only the production of the head has to be carried out in a single additive production step. However, it is also possible, for example, for only a head of an instrument to be produced additively and for the head then to be joined to a prefabricated shaft in another way, for example by friction welding, laser welding or the like.

Thus, according to the invention, it has been made possible for the first time to carry out large-scale industrial production of medical instruments by means of additive methods. The use of such methods has hitherto not been considered in the medical sector, since additive production methods are in most cases only used for manufacture of prototypes or for individual manufacture.

By means of the method provided according to the invention, it is thus possible, from very different materials (titanium or titanium alloys, ceramic, plastic, steel, hard metal or the like), to generate any desired geometries, in particular for heads of medical instruments which have a high degree of strength and permit a configuration independently of the limitations imposed by tools.

The method according to the invention is also suitable for re-working additively produced areas of the medical instrument by means of a subtractive method. For example, it is thus possible to sharpen or calibrate the cutting edges, for example of a head of a milling cutter, by means of a subtractive laser technique. This can also be done, for example, in order to improve the concentric running of a rotary medical instrument.

The invention is described below on the basis of an illustrative embodiment and with reference to the drawing, in which:

FIG. 1 shows, as starting material for a combined production method, a semi-finished product 1 in the form of a cylindrical pin or wire.

In a next work step, the semi-finished product is machined to cut away material, so as to generate a shaft 2 with a clamping region 3 and with a neck 4. This intermediate product is then completed by means of an additive method in which material is applied in layers to generate a head 5 provided with cutting edges.

If necessary, the cutting edges can be sharpened by means of a subtractive method, for example by laser ablation.

Figure 1:
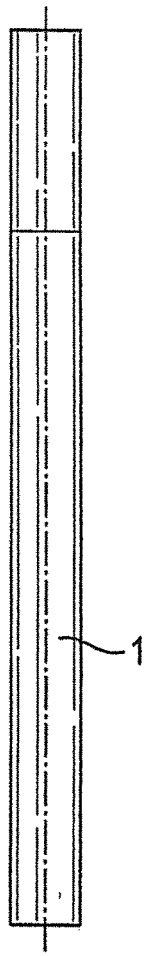
FIG. 1 shows a schematic side view of a semi-finished product to be used.
Figure 2:
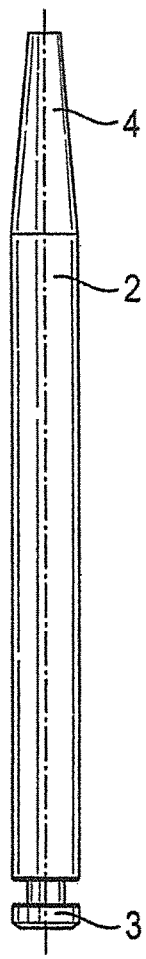
FIG. 2 shows a production step in the production of a shaft.
Figure 3:
FIG. 3 shows a completed additive medical instrument in the form of a drill or milling cutter.
Figure 4:
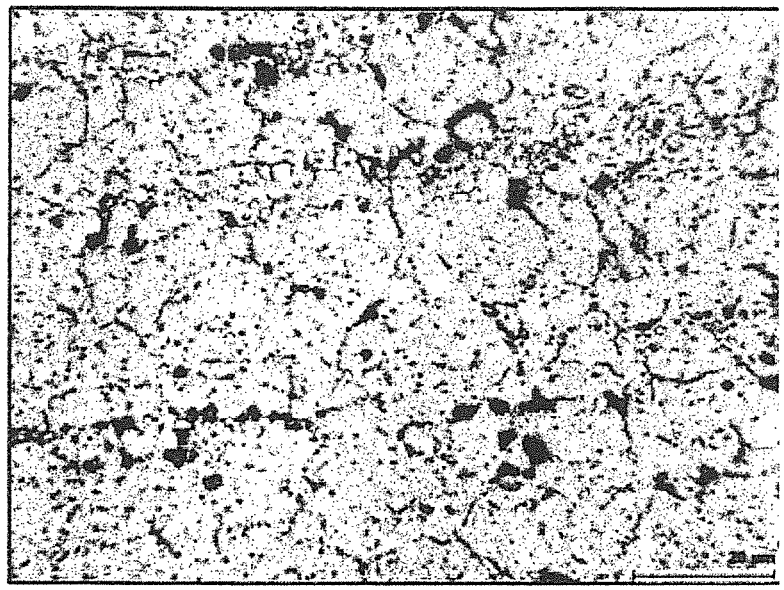
FIG. 4 shows a micrograph of the typical structure of drawn steel with subsequent heat treatment.
Figure 5:
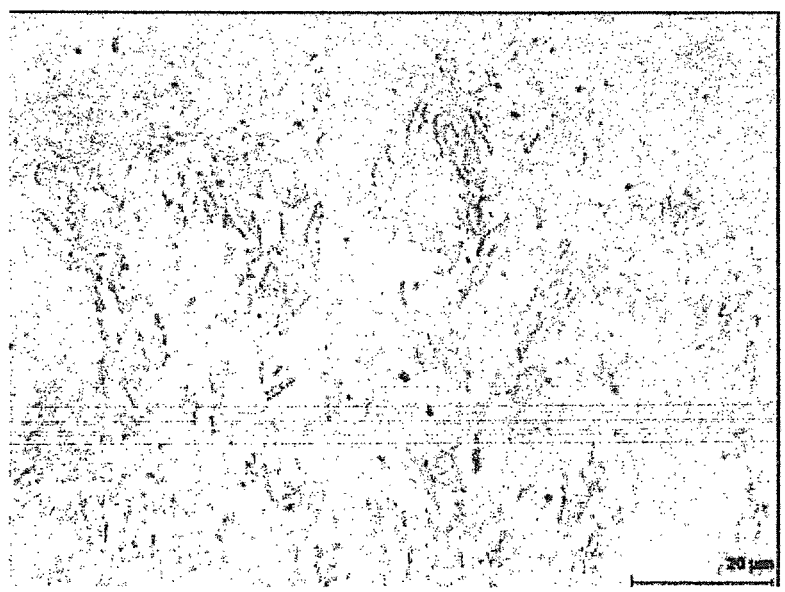
FIG. 5 shows a micrograph of a material generated by an additive laser fusion method.

FIGS. 4 and 5 show micrographs allowing a comparison between a conventionally generated material and a material generated by means of an additive method.

The micrograph shown in FIG. 4 is that of a conventionally produced material which has the typical structure of drawn steel with subsequent heat treatment. The carbides arranged lengthwise in the martensitic matrix can be clearly seen.

FIG. 5, by contrast, shows a micrograph of a material generated by means of an additive laser fusion method. The micrograph clearly shows a coarse, martensitic structure with fine carbide dispersions, which have no particular arrangement. In additively produced workpieces, it proves advantageous that these do not form hardening cracks, as is the case in conventionally generated workpieces.

The invention claimed is:

1. A method for producing a medical instrument, comprising:
   producing, by cutting material from a semi-finished product, a shaft including a clamping region and at least part of a head including cutting edges,
   additively generating at least part of the head of the instrument;
   performing the additively generating with a rotation axis of the instrument aligned vertically;
   reworking at least part of the head with a subtractive method;
   using the subtractive method to perform at least one chosen from sharpening cutting edges and improving concentric running of the instrument.

2. The method as claimed in claim 1, wherein the additively generating is performed using a selective laser application method, a selective laser sintering method or an electron beam welding method.

3. The method as claimed in claim 1, wherein at least the additively generated part of the instrument is made of steel, ceramic, hard metal, titanium, titanium alloy or plastic.

4. The method as claimed in claim 1, wherein the subtractive method is at least one chosen from a laser ablation method and a cutting method.

5. The method as claimed in claim 1, wherein the instrument is at least one chosen from a dental drill, a milling cutter, a grinding instrument, a sonic tip and a saw blade.

6. The method as claimed in claim 1, wherein the instrument is a dental instrument.

\* \* \* \* \*